(12) United States Patent
Lambert et al.

(10) Patent No.: US 7,312,346 B2
(45) Date of Patent: Dec. 25, 2007

(54) METHOD OF PURIFYING HYDROXYALKYL AMIDE

(75) Inventors: Timothy L. Lambert, Waterbury, CT (US); E. Brian Fox, Monroe, CT (US)

(73) Assignee: Crompton Corporation, Middlebury, CT (US)

( * ) Notice: Subject to any disclaimer, the term of this patent is extended or adjusted under 35 U.S.C. 154(b) by 477 days.

(21) Appl. No.: 10/712,830

(22) Filed: Nov. 12, 2003

(65) Prior Publication Data

US 2005/0097813 A1    May 12, 2005

(51) Int. Cl.
*C11C 3/00*    (2006.01)
(52) U.S. Cl. .......................... 554/68; 554/70
(58) Field of Classification Search .......... 554/68, 554/70
See application file for complete search history.

(56) References Cited

U.S. PATENT DOCUMENTS

| 4,208,293 | A | | 6/1980 | Zaweski |
| 4,729,769 | A | | 3/1988 | Schlicht et al. |
| 4,960,530 | A | | 10/1990 | Everett et al. |
| 5,523,431 | A | | 6/1996 | Sköld |
| 6,034,257 | A | * | 3/2000 | Oftring et al. ............... 554/69 |

FOREIGN PATENT DOCUMENTS

GB    2252555 A    8/1992
WO    WO 96/40619    12/1996

* cited by examiner

*Primary Examiner*—Deborah D. Carr
(74) *Attorney, Agent, or Firm*—Jaimes Sher

(57) ABSTRACT

A method for purifying hydroxyalkyl amide of residual alkanolamine by using nonpolar solvent, an acidic pH, salt solutions and an elevated temperature.

70 Claims, No Drawings

METHOD OF PURIFYING HYDROXYALKYL AMIDE

BACKGROUND OF THE INVENTION

1. Field of the Invention

This invention relates to a method for producing a friction-modifying fuel or lubricant additive composition that contains a decreased level of reactant components.

2. Description of Related Art

Fuel economy standards mandated by the federal government have resulted in efforts by the automotive industry to improve the fuel economy of motor vehicles. One way to reduce fuel consumption is by reducing friction in particular areas of the engine, e.g., bearings, valve trains, pistons, rings, water and oil pumps. A moderate decrease in the friction of these components will be reflected in a corresponding fuel economy improvement. Therefore, there has been an ongoing search for friction modifier compositions that will decrease friction in these key areas and thus improve fuel economy.

Various types of additives have been used as friction modifiers. Some of the more commercially and conventionally used friction modifiers are fatty acid esters, fatty acid amides and fatty acid ester-amides. U.S. Pat. No. 4,960,530 discloses an example of a lubricant additive and composition that can reduce friction.

Hydroxyalkyl amides have been used extensively as friction modifiers. U.S. Pat. No. 4,729,769 discloses a fatty acid amide detergency additive which is the reaction product of a $C_6$-$C_{20}$ fatty acid ester and a mono- or di-(hydroxy hydrocarbonyl) amine.

U.S. Pat. No. 4,208,293 discloses a lubricating oil adapted for use as a crankcase lubricant in internal combustion engines containing a friction-reducing amount of a fatty acid amide or ester of diethanolamine.

Although the production of hydroxyalkyl amides as friction modifiers for fuel additives amongst other things has been quite extensive, most of processes for producing hydroxyalkyl amides produce a composition that retains a certain percentage of unreacted alkanolamine, together with other undesirable residuals. Certain end-use users desire hydroxyalkyl amides as friction modifying fuel additives with a decreased level and/or an undetectable level of alkanolamine and/or residual catalyst. Therefore, it would be advantageous to provide a process for producing hydroxyalkyl amides with a low level or an undetectable level of alkanolamine and/or residual catalyst.

The most common and simplest method of purifying hydroxyalkyl amides is through aqueous washes and the successive removal of the aqueous phase which results from the separation of the mixture into an organic and aqueous phase.

Typically, aqueous washes of hydroxyalkyl amide compositions result in low degrees of impurity removal while at the same time create an undesirable amount of waste water. In addition, aqueous washes can result in a decreased level of aqueous phase separation. It is important to have as great a level of aqueous phase separation as possible and therefore as little retained water in the organic phase because at high levels of retained water, more impurities are retained in the organic phase, more energy is required to dry the product due to the increased mass of water to be removed, foaming of the product results during the drying step and more aqueous waste is generated.

Therefore, it would be advantageous to provide a method for purifying hydroxyalkyl amide through use of an aqueous wash that would avoid the above-described problems and yet still provide for good separation of the organic and aqueous phases.

SUMMARY OF THE INVENTION

It is an object of the invention to provide a method of making a hydroxyalkyl amide composition with a decreased level of alkanolamine.

It is a further object of the invention to provide a method of making a hydroxyalkyl amide composition with a decreased level of residual catalyst.

It is still further an object of the invention to provide a liquid engine fuel or lubricant composition containing a friction-modifying or lubricity amount of hydroxyalkyl amide composition that possesses a decreased level of residual alkanolamine and/or residual catalyst.

In keeping with these and the other objects of the invention, there is provided a method for the purification of the reaction product mixture of at least one alkanolamine and at least one ester and/or fatty natural material, optionally, in the presence of catalyst, said reaction product mixture containing a significant amount of residual alkanolamine and/or residual catalyst, which comprises providing said reaction product mixture, and either simultaneously or sequentially, in any particular order:

a) adding at least one non-polar solvent to said reaction product mixture;

b) heating said reaction product mixture to a desired extraction temperature;

c) providing aqueous salt solution to said reaction product mixture;

d) adjusting the pH of the reaction product mixture to below about 7.0;

e) allowing separation of the reaction product mixture into an organic phase and an aqueous phase after completion of steps (a)-(d); and, f) removing the aqueous phase to produce a hydroxyalkyl amide composition with a reduced level of residual alkanolamine and/or residual catalyst.

Furthermore, in accordance with the invention, there is provided a liquid engine fuel or lubricant composition comprising a major amount of liquid hydrocarbon fuel and a minor amount of a hydroxyalkyl amide composition with a reduced level of residual alkanolamine and/or residual catalyst obtained by the foregoing process.

DETAILED DESCRIPTION OF THE INVENTION

The primary and/or secondary alkanolamine of the current invention has the general formula RNHR' wherein R is hydroxyalkyl of from 2 to about 10 carbon atoms and R' is hydrogen, alkyl of from 1 to about 10 carbon atoms or hydroxyalkyl of from 2 to about 10 carbon atoms. Preferably, the alkanolamine will be a dialkanol amine, most preferably diethanolamine, although other primary and secondary alkanolamines can be used. Mixtures of various primary and secondary alkanolamines can be utilized as well. Examples of primary and secondary alkanolamines are ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and mixtures thereof.

The amount of primary and/or secondary alkanolamine will be dependent on the desired hydroxyalkyl amide, but generally the molar ratio of primary and/or secondary alkanolamine to ester will be preferably from about 0.75:1 to about 1.25:1, more preferably from about 0.90:1 to about 1.10:1, and most preferably from about 0.95:1 to about 1.05:1.

The parent acid of the ester can be a fatty acid derived from natural materials such as canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof. Preferably, the ester will be a fatty acid methyl ester or mixture of fatty acid methyl esters, preferably, the parent acid of the ester is a fatty acid derived from coconut oil and the parent alkanol of the ester is methanol, although any methyl ester of the above-described natural materials can be used. In addition, instead of, or in combination with the ester and alkanolamine, a fatty acid can be used. Examples of fatty acids that can be used alone or in combination with ester are the same or different fatty acids that are the parent acid of the ester. If a fatty acid is used alone or in combination with the ester, fatty natural material and alkanolamine, the reaction products then can be fatty acid amide as well as water. The process of the current invention is preferably conducted in the absence of water to prevent unwanted side reactions such as the hydrolysis of the ester and amide to acid and alcohol or amine.

In addition, instead of, or in combination with the ester and alkanolamine, the fatty natural materials themselves can be used. Examples of fatty natural materials that can be used alone or in combination with ester are the same as the sources for the parent acid of the esters listed above, such as straight fatty oils, e.g., coconut oil, palm oil, canola oil and the other natural materials listed above. If a fatty natural material is used alone or in combination with the ester and alkanolamine, the reaction products then can be fatty acid amide as well as glycerin. The process of the current invention is preferably conducted without glycerin. The parent acid of the ester contains from about 4 to about 22 carbon atoms and the parent alkanol of the ester contains from 1 to about 10 carbon atoms.

Fatty acid esters are known to encompass esterified carboxylic acids such as monoglycerides, diglycerides and triglycerides, as well as straight chain carboxylic acids that have been esterified. Polymeric fatty acid esters are also contemplated as fatty acid esters. Examples of polymeric fatty acid esters are esters of dimer and trimer acids such as Arizona Chemicals Century 1156, and Unidyne 14 and Unidyne 60 and Uniqema's Pripol 1017 or 1006 and the like. Various combinations and mixtures of the above-described natural matter can be used.

The amount of ester and/or fatty natural material will be present in the same molar ratio as that of the alkanolamine to ester as described above.

The parent acid of the ester used in the current invention is generally made from a fatty acid. The fatty acid used to make the fatty acid ester and preferably the fatty acid methyl ester can vary depending on the desired fatty acid ester but can include acids such as, butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15,19-docosapentaenoic, docosahexaenoic, lignoceric, tetracosenoic and mixtures thereof.

The alkanolamine and ester can be reacted, optionally in the presence of catalyst. The catalyst can be present either in concentrate or in solvent. Suitable solvents for the catalyst can include any volatile alcohol containing up to about six carbon atoms such as methanol, ethanol, isopropanol, n-propanol, butanol, t-butanol, sec-butanol, normal or branched pentanols and normal or branched hexanols. If a solvent is used, it can be present in any amount necessary to solvate the catalyst, which is preferably a solution of from about 1 to about less than 100, more preferably from about 10 to about 50 and most preferably from about 20 to about 30 wt. percent of catalyst concentrate in solvent. Generally, a basic catalyst will be used, such as an alkoxide and/or carbonate catalyst, preferably a metal alkoxide and/or a metal carbonate catalyst. Examples of suitable metal alkoxide and metal carbonate catalysts can include sodium methoxide, sodium ethoxide, sodium propoxide, potassium methoxide, potassium ethoxide, potassium propoxide, sodium or potassium butoxide, sodium or potassium pentoxide, sodium or potassium hexanoate, sodium carbonate, potassium carbonate, cesium carbonate, calcium carbonate, strontium carbonate, barium carbonate and mixtures thereof, with sodium methoxide being most preferred. The amount of metal alkoxide or metal carbonate catalyst will be in a catalytically effective amount which can vary greatly but will preferably be from about 0.05 to about 1.00, more preferably from about 0.25 to about 0.75 and most preferably from about 0.4 to about 0.6 wt. percent of the reaction product mixture. In addition, organic catalysts such as tetraalkyl ammonium hydroxide can be used as well as ethylisopropylamines, Hunig's base (diisopropylethyl amine), DBU (1,8-diazabicyclo[5.4.0]undec-7-ene, DBN (1,5-diazabicyclo[4.3.0]non-5-ene, guanidine, pentamethyl guanidine. The amount of organic catalyst can vary greatly but will preferably be from about 0.05 to about 1.00, more preferably from about 0.25 to about 0.75, and most preferably from about 0.40 to about 0.60 wt. percent of the reaction product mixture.

The current invention can reduce the level of alkanolamine and/or catalyst in a hydroxyalkyl amide composition through a combination of four factors.

First of all, the hydroxyalkyl amide composition can be exposed to non-polar solvent by providing non-polar solvent to the reaction product mixture of alkanolamine, ester and/or fatty natural material and optionally catalyst. The non-polar solvent facilitates the separation of the reaction product mixture into an organic layer and an aqueous layer. The non-polar solvent can be at least one such as benzene and toluene, and can also be any non-polar solvent selected from groups of solvents such as xylenes, aromatic mixed solvents, pentanes, hexanes, heptanes, octanes, nonanes, decanes and petroleum distillate fractions. Examples of aromatic mixed solvents can be aromatic 100, aromatic 150, Aromatic 150 ND, alkyl naphthalenes, cumene, alkyl benzenes]. Examples of petroleum distillate fractions can be petroleum ether, ligroin, napthas, gasoline fractions, kerosene and mixtures thereof. Aromatic 150 is preferred. The amount of non-polar solvent can be preferably from about 95 to about 5, more preferably from about 50 to about 10 and most preferably from about 30 to about 15 wt. percent of the reaction product mixture.

Second of all, the reaction product mixture described above can be heated to a specific extraction temperature. The extraction temperature is dependent on the particular hydroxyalkyl amide in the hydroxyalkyl amide composition.

The extraction temperature is the temperature at which about it has been found that the reaction product mixture which was previously mostly homogenous, begins to break into a heterogenous system comprising an aqueous phase and an organic phase, the organic phase containing the hydroxyalkyl amide. Preferably, the extraction temperature can be above about 50°, more preferably above about 60°, and most preferably above about 70° C.

Third of all, an aqueous salt solution can be provided to the reaction product mixture wherein the salt of the salt solution is at least one monovalent or divalent salt of a mineral acid. Examples of suitable mineral acids are hydrochloric acid, sulfuric acid and nitric acid, phosphoric acid. In addition, the salt solution can contain any known or commercially available salt, e.g., NaCl, KCl, $K_2SO_4$, $KHSO_4$, $Na_2SO_4$, $NaHSO_4$, $KH_2PO_4$, $K_2HPO_4$, $NaH_2PO_4$, $Na_2HPO_4$, $CaSO_4$, $MgSO_4$, $CaCl_2$. The amount of aqueous salt solution can preferably be from about 90 to about 0.1, more preferably from about 50 to about 5 and most preferably from about 30 to about 10 wt. percent of the reaction product mixture. The aqueous salt solution can be one of the materials which provides the water for the successive aqueous washes which can be utilized in the current invention. Other sources of aqueous material can also be used in conjunction with the aqueous salt solution such as deionized water, distilled water and tap water, as well as any clarified water source. It is the cumulative effect of all 4 steps, including the aqueous washes which produce the purest hydroxyalkyl composition, any one of which of these steps can be repeated as necessary or desired to effect further impurity removal.

Fourth of all, the reaction product mixture can be separated into the said phases effectively by adjusting the pH of the solution to below the PKa of the alkanolamine, e.g., a pH less than 8. Preferably, the pH can be adjusted below about 7, and most preferably below about 6.5. This can be accomplished by using one or more acids such as hydrochloric acid, sulfuric acid, phosphoric acid, or nitric acid, organic acids with pKa's less than about 6. The amount of acid varies according to the amount of residual alkanolamine and the specific acid used. Generally, it is preferable that sufficient acid is added to lower the pH to the above-proscribed levels.

Alone, any one of the four said factors can provide some level of separation of the phases and thus greater removal of residual alkanolamine and/or residual catalyst and other impurities, but it is the cumulative effect of all four said factors through successive aqueous washes which results in the dramatic decrease of residual alkanolamine, residual catalyst and other impurities in the current invention.

Preferably, the various steps of providing solvent, heating, providing aqueous salt solution and adjusting the pH can be repeated one or more times through successive aqueous washes if desired to further improve the purity of the hydroxyalkyl amide composition. These steps can be conducted in any particular sequence or simultaneously to yield the hydroxyalkyl amide composition. This can include repeating one step one or more times before proceeding to the next step.

The current invention can further comprise employing the above-described reactants for producing a hydroxyalkyl amide composition in the presence of at least one metal silicate absorbent or treating the hydroxyalkyl amide composition produced by the above-described reactants with metal silicate absorbent. Suitable examples of metal silicate absorbents include any metal silicate absorbent wherein the metal is from Group IA, IIIA or Group IIIA of The Periodic Table. Examples of preferable metals include magnesium, calcium, aluminum, barium and sodium with magnesium being the most preferable metal. Suitable metal silicate absorbents are of the general formula $xMO:ySiO_2:zH_2O$ wherein, as described above, M is any Group IA, IIA or Group IIIA metal, x and y are in a molar ratio of from about 1.5:1 to about 1:3.6 and z is equal to x. The most preferable metal silicate absorbents are magnesium silicate absorbents of the above formula, wherein x is 1, y is 2.6 and z is 1. The metal silicate absorbent can be provided preferably from about 20 to about 0, more preferably from about 10 to about 1, and most preferably from about 5 to about 2 wt. percent of hydroxyalkyl amide composition.

The resultant hydroxyalkyl amide composition can be vacuum stripped for residual water at from about 50 to about 110° C. and at less than about 100 mm Hg until the organic phase is dry. Other drying steps can be employed in place of or in addition to vacuum stripping such as exposure to an inert gas, molecular sieves The hydroxyalkyl amide which is produced by the reaction of primary and/or secondary alkanolamine and ester and/or fatty natural material can be any amide such as a monofunctional or difunctional hydroxyalkyl amide but preferably a hydroxyalkyl fatty acid amide, more preferably a N,N,-Bis(2-hydroxyethyl)fatty acid amide, and most preferably a N,N-Bis(2-hydroxyethyl) cocoamide.

The hydroxyalkyl amide reaction product of the alkanolamine, ester and/or fatty natural material and catalyst can be reacted with metal silicate under agitation alone and/or in combination with a vacuum of reduced pressures as described above. The resultant hydroxyalkyl amide reaction product can be separated by any known process such as decanting, filtration, distillation, recrystalization and the like. If the separation is done by filtration, any conventional or known filtration process can be used. This can be followed by filtering the reaction product and a filter aid over a filter, preferably a small micron size filter, e.g., a one micron filter to obtain the purified hydroxyalkyl amide composition. Preferably the filtration aid is one such as Celite® 545 (95% $SiO_2$), diatomaceous earth, diatomite, kieselguhr, soda ash flux calcined and the like. The amount of filtration aid will vary greatly but preferably can range from about 0 to about 10, more preferably from about 1 to about 5 and most preferably from about 2 to about 3 wt. percent. The metal silicate absorbent will preferably remain in the solid state when mixed with the reaction product of alkanolamine, ester and/or fatty natural material and catalyst. The hydroxyalkyl amide composition can pass through the filter along with residual ester. The residual alkanolamine remains with the solid metal silicate absorbent.

It will be understood by those skilled in the art that the foregoing hydroxyalkyl amide composition constitutes a complex mixture of compounds including fatty acid amides, as well as fatty acid esters, fatty acid ester-amides, unreacted reactants, free fatty acids, glycerol, and partial fatty acid esters of glycerol (i.e., mono- and di-glycerides). Both primary and secondary hydroxyalkyl fatty acid amides can be produced by the current invention. Preferably, the hydroxyalkyl amide composition produced by this invention will contain from about 10 to about 99, more preferably from about 40 to about 90, and most preferably from about 70 to about 80 wt. percent of monofunctional or difunctional hydroxyalkyl amide.

Producing hydroxyalkyl amide in accordance with the current invention has been found to reduce unreacted alkanolamine to an advantageously low level, for example preferably less than about 0.5, more preferably less than about 0.2, and most preferably less than about 0.1 wt. percent of the hydroxyalkyl amide composition. Furthermore, producing hydroxyalkyl amide in accordance with the current invention has been found to reduce residual catalyst levels to an advantageously low level, for example preferably less than about 0.3, more preferably less than about 0.15, and most preferably less than about 0.05 wt. percent of the hydroxyalkyl amide composition. Alternatively stated, the level of residual catalyst in the hydroxyalkyl amide composition is reduced by at least preferably, 50, more preferably 75, and most preferably 99 percent. The hydroxyalkyl amide composition of this invention, due to its especially low residual level of alkanolamine and/or catalyst is especially useful as a friction-modifying additive or lubricity aid for engine fuels, in particular gasoline engines, diesel engines, jet engines and the like, or lubricants.

The hydroxyalkyl amide composition as prepared and described above can be used as a friction reduction additive or lubricity aid for engine fuels, e.g., gasoline and diesel fuels, or lubricants. Preferably, it will be added to a liquid engine fuel composition or lubricant in a friction-modifying or lubricity aid amount. A friction-modifying or lubricity aid amount will vary greatly depending on its intended use. Preferably, a friction-modifying or lubricity aid amount will range from about 10 to about 1000, more preferably from about 25 to about 500 and most preferably from about 50 to about 100 ppm in fuels while lubricants, which generally require higher additive treats, preferably 0.1 to about 1.0, or more preferably 0.20 to 0.75 and most preferably from about 0.25 to about 0.5 wt % will be used. Fuels to which the above-described hydroxyalkyl amide composition can be added include, for example, gasoline, diesel, kerosene, jet fuels, and the like. Lubricants to which the above-described hydroxyalkylamide composition can be added include both synthetic and mineral based lubricants using base fluids from the various API base oil categories, Group I, Group II, Group III, Group IV or Group V. Various other components can be added to the fuel or lubricant additive composition in addition to the hydroxyalkyl amide composition. These additional components are known to persons skilled in the art and will not be discussed herein.

The process of this invention can be carried out over a wide range of temperatures, preferably from about 40° to about 150° C., more preferably from about 50° to about 90° C. and most preferably from about 60° to about 70° C. The duration of the reaction as well can be conducted over a broad range. Preferably, the invention can be carried out for a period of from about 30 minutes to 24 hours, more preferably from about 3 to about 12 hours and most preferably from about 4 to about 8 hours. The reaction can be conducted at any pressure but preferably at reduced pressure. Suitable reduced pressures can range from about 0.5 to about 500 and preferably from about 10 to about 100 torr. The reduced pressure allows for the simultaneous removal of methanol from the reaction medium which helps speed the reaction.

The reaction vessel used in the process of the invention can be any conventional or known vessel, preferably an agitated vessel and more preferably a stirred tank reactor. The process of the invention can be conducted in batch or in continuous processes.

The following table illustrates the effectiveness of using the above-described non-polar solvent, salt solution, pH adjustment and increased temperature to remove alkanolamine and water (Examples 14) as opposed to the presence of alkanolamine and water in a hydroxyalkyl amide composition that has not been exposed to a combination of non-polar solvent, salt solution, pH adjustment and increased temperature (Comparative Examples 1-3).

TABLE 1

| Example Number | Extracting Phase | pH | Solvent | Retained water g HOH/g cocoamide | Residual DEA, wt % | Residual Na, ppm |
|---|---|---|---|---|---|---|
| Example 1 | water | 3.8 | 20% aromatic 150 | 0.13 | 0.00 | 377 |
| Example 2 | 10% aqueous NaCl | 5.7 | 20% aromatic 150 | 0.03 | 0.00 | 470 |
| Example 3 | Water | 5.7 | 30% Toluene | 0.12 | 0.31 | 100 |
| Example 4 | 10% aqueous $Na_2SO_4$ | 5.0 | 34% Toluene | 0 | 0.08 | 4 |
| Comparative Example 1 | water | 7.0 | none | 0.49 | 1.80 | 1257 |
| Comparative Example 2 | 10% aqueous NaCl | 7.0 | none | 0.19 | 0.14 | 971 |
| Comparative Example 3 | water | 4.5 | none | 0.36 | 0.13 | 533 |

Initial sodium = 2678 ppm
Initial DEA = 1.2 wt %

The following examples, whose results are detailed in Table 1 above, are illustrative of the invention.

EXAMPLE 1

167.35 g of crude cocoamide was charged to a stirred tank reactor affixed with agitation, pH measurement, and vacuum stripping capabilities and a bottom out valve. 34.22 g of aromatic 150 were added to the cocoamide. The mixture was heated under agitation for 90 minutes and then 147.5 g of deionized water was added and a pH probe was inserted into the reactor. The pH indicated was 10.5. The pH was adjusted to 3.8 and the mixture was heated to 80° C. The agitation was then stopped and the mixture was allowed to settle. 127.5 g of aqueous phase was recovered. 112.03 g of NaCl was added and the mixture was reheated under agitation to 80° C. The mixture was allowed to settle again. 124.75 g of aqueous phase were recovered. The separated organic phase had 101.62 g of a 10% NaCl solution added thereto and was allowed to stir. Agitation was stopped and the mixture was allowed to settle. 99.1 g of aqueous phase was recovered and separated. 3.3 g of a synthetic magnesium silicate absorbent was added under agitation. The resultant mixture was vacuum stripped for 105 minutes and then the vacuum was broken and 1.2 g of Celite 545 (95% $SiO_2$) was added. The resultant mixture was filtered to yield 132.26 g of sample. The sample was tested for retained water, residual diethanolamine and residual sodium as is shown in Table 1.

EXAMPLE 2

111.4 g of crude cocoamide was charged to a stirred tank reactor affixed with agitation, pH measurement, and vacuum stripping capabilities, and a bottom out valve. 23.11 g of a 10% NaCl aqueous solution was added under agitation. A pH probe was inserted into the reactor and a pH of 9.7 was measured. The pH was adjusted to 4.4 under agitation over 10 minutes. 21.9 g of aromatic 150 solvent was added under agitation. The agitation was stopped and the mixture was allowed to settle into two distinct layers. 19.23 g of aqueous phase was recovered. 22.45 g of a 10% NaCl aqueous solution was added under agitation over 20 minutes and then the agitation was stopped and 20.4 g of aqueous phase was removed from the reaction mixture. 23.12 g of a 10% NaCl aqueous solution was added under agitation over 10 minutes and then agitation was stopped and the reaction mixture was allowed to settle and 22.37 g of aqueous phase was recovered. 1.99 g of a synthetic magnesium silicate was added over 40 minutes under agitation. The resultant mixture was vacuum stripped for 37 minutes and then the vacuum was broken and 1 g of Celite 545 (95% $SiO_2$) was added and mixed at 100° C. and then filtered over a 1 micron filter to yield 83.48 g of sample. The sample was tested for retained water, residual diethanolamine and residual sodium as is shown in Table 1.

EXAMPLE 3

162.5 g of crude cocoamide was charged to a stirred tank reactor affixed with agitation, pH measurement, and vacuum stripping capabilities, and a bottom out valve. 52.6 g of deionized water and 50 grams of toluene were added under agitation. A pH probe was inserted into the reactor and a pH of 10.6 was measured. The pH was adjusted to 5.7 under agitation over 10 minutes. The agitation was stopped and the mixture was allowed to settle into two distinct layers. 29.9 g of aqueous phase was recovered. 34.0 g of deionized water was added under agitation over 10 minutes and then the agitation was stopped and 31.35 g of aqueous phase was removed from the reaction mixture. 29.91 g of a deionized water was added under agitation over 10 minutes and then agitation was stopped and the reaction mixture was allowed to settle and 35.1 g of aqueous phase was recovered. The resultant mixture was vacuum stripped for 92 minutes at a maximum temperature of 95 C. The resultant product was filtered over a 1 micron filter. The sample was tested for retained water, residual diethanolamine and residual sodium as is shown in Table 1.

EXAMPLE 4

118.2 g of crude cocoamide was charged to a stirred tank reactor affixed with agitation, pH measurement, and vacuum stripping capabilities, and a bottom out valve. 46.11 g of a 10% $Na_2SO_4$ aqueous solution and 40.43 g of toluene were added under agitation. A pH probe was inserted into the reactor and a pH of 12.4 was measured. The pH was adjusted to 5.0 under agitation over 10 minutes. The agitation was stopped and the mixture was allowed to settle into two distinct layers. 53.85 g of aqueous phase was recovered. 24.4 g of a 10% $Na_2SO_4$ aqueous solution was added under agitation over 10 minutes and then the agitation was stopped and 21.09 g of aqueous phase was removed from the reaction mixture. 21.38 g of a 10% $Na_2SO_4$ aqueous solution was added under agitation over 10 minutes and then agitation was stopped and the reaction mixture was allowed to settle and 20.93 g of aqueous phase was recovered. The resultant product was vacuum stripped for 72 minutes at a maximum temperature of 95 C. and then filtered over a 1 micron filter. The sample was tested for retained water, residual diethanolamine and residual sodium as is shown in Table 1.

COMPARATIVE EXAMPLE 1

115.8 g of crude cocoamide was charged to a stirred tank reactor affixed with agitation, pH measurement and vacuum stripping capabilities and a bottom out valve. The cocoamide was heated to 80° C. over 30 minutes. 115 ml of distilled water were added to the reactor and a pH probe was inserted which indicated a pH of 10.7. The mixture was heated to 85° C. under agitation and the pH was neutralized to 7 with 3 molar HCl acid. The agitation was stopped and the mixture was allowed to settle into a separate organic phase and an aqueous phase. 58.3 g of the aqueous phase was removed. The organic phase was then vacuum stripped at 60 mm and at 95° C. for 30 minutes. The resultant product was tested for retained water, residual diethanolamine and residual sodium as is shown in Table 1.

COMPARATIVE EXAMPLE 2

The resultant product of Comparative Example 1 had 93 ml of distilled water added under agitation. The mixture was heated to 85° C. and then the agitation was stopped and the mixture was allowed to settle, 90 ml of distilled water was added and the pH was adjusted to 6.6 and 130.5 g of aqueous phase was recovered. The pH was readjusted to 6 and an additional 12 ml of aqueous phase was recovered. 5 ml of a saturated NaCl solution was added and an additional 28 ml of aqueous phase was recovered. An additional 5 ml of saturated NaCl solution was added. The mixture was heated under agitation and while being vacuum stripped for 50 minutes. The vacuum was broken and 0.9 g of a synthetic magnesium silicate was added along with 1 g of Celite 545 (95% $SiO_2$). The agitation was stopped and the resultant mixture was filtered at 100° C. over a 1 micron filter over four minutes. 67.85 g of sample was recovered. The sample was tested for retained water, residual diethanolamine and residual sodium as is shown in Table 1.

COMPARATIVE EXAMPLE 3

128.24 g of crude cocoamide was charged to a stirred tank reactor with agitation, pH measurement and vacuum stripping capabilities and a bottom out valve. The cocoamide was heated over a period of 25 minutes to 85° C. and 129 g of deionized water was added and a pH probe was inserted that indicated a pH of 9.8. The pH was adjusted to 3.5 with 3 molar HCl acid. The agitation was stopped and the mixture was allowed to separate into an organic phase and an aqueous phase. 78.75 g of aqueous phase was removed. 3.6 g of a synthetic magnesium silicate was added under agitation. The resultant mixture was vacuum stripped at 330 mm and slowly decreased to 48 mm over 60 minutes. The resultant mixture was filtered at 100° C. over a 1 micron filter, yielding 103.05 g of product. The product was tested for retained water, residual diethanolamine and residual sodium as is shown in Table 1.

What is claimed is:

1. A method for the purification of the reaction product mixture of at least one alkanolamine and at least one ester and/or fatty natural material, optionally, in the presence of catalyst, said reaction product mixture containing a significant amount of residual alkanolamine and/or residual catalyst, which comprises providing said reaction product mixture, and either simultaneously or sequentially, in any particular order:
(a) adding at least one non-polar solvent to said reaction product mixture;
(b) heating said reaction product mixture to a desired extraction temperature;
(c) providing aqueous salt solution to said reaction product mixture;

(d) adjusting the pH of the reaction product mixture to below 7.0;
(e) allowing separation of the reaction product mixture into an organic phase and an aqueous phase after completion of steps (a)-(d); and,
(f) removing the aqueous phase to produce a hydroxyalkyl amide composition with a reduced level of residual alkanolamine and/or residual catalyst.

2. The method of claim 1 wherein the alkanolamine is of the general formula RNHR' wherein R is hydroxyalkyl of from 2 to about 10 carbon atoms and R' is hydrogen, alkyl of from 1 to about 10 carbon atoms or hydroxyalkyl of from 2 to about 10 carbon atoms.

3. The method of claim 2 wherein the alkanolamine is selected from the group consisting of ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and mixtures thereof.

4. The method of claim 1 wherein the parent acid of the ester contains from about 4 to about 22 carbon atoms and the parent alkanol of the ester contains from 1 to about 10 carbon atoms.

5. The method of claim 4 wherein the ester is a fatty acid methyl ester or mixture of fatty acid methyl esters.

6. The method of claim 4 wherein the parent acid of the ester is a fatty acid derived from canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof.

7. The method of claim 1 wherein the fatty natural material is selected from the group consisting of canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof.

8. The method of claim 6 wherein the parent acid of the ester is a fatty acid derived from coconut oil and the parent alkanol of the ester is methanol.

9. The method of claim 4 wherein the parent acid of the ester is selected from the group consisting of butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15, 19-docosapentaenoic, docosahexaenoic, lignoceric, tetracosenoic and mixtures thereof.

10. The method of claim 9 wherein the parent alkanol of the ester is methanol.

11. The method of claim 1 wherein the catalyst is a basic catalyst.

12. The method of claim 11 wherein the basic catalyst is metal alkoxide and/or metal carbonate catalyst.

13. The method of claim 12 wherein the metal alkoxide and/or metal carbonate is selected from the group consisting of sodium methoxide, sodium ethoxide, sodium propoxide, potassium methoxide, potassium ethoxide, potassium propoxide, sodium or potassium butoxide, sodium or potassium pentoxide, sodium or potassium hexanate, sodium carbonate, potassium carbonate, cesium carbonate, calcium carbonate, strontium carbonate, barium carbonate and mixtures thereof.

14. The method of claim 11 wherein the basic catalyst is an organic catalyst selected from the group consisting of tetraalkyl ammonium hydroxide, ethylisopropyl amines, Hunig's Base (diisopropyl ethyl amine), DBU (1,8-diazabicyclo[5.4.0]undec-7-ene), DBN (1,5-diazabicyclo[4.3.0]non-5-ene), guanidine, and pentamethyl guanadine.

15. The method of claim 1 wherein the catalyst is present in an amount of from about 1 to about less than 100 wt. percent of catalyst concentrate in solvent.

16. The method of claim 15 wherein the catalyst is present in an amount of from about 10 to about 50 wt. percent of catalyst concentrate in solvent.

17. The method of claim 16 wherein the catalyst is present in an amount of from about 20 to about 30 wt. percent of catalyst concentrate in solvent.

18. The method of claim 13 wherein the metal alkoxide and/or metal carbonate catalyst is present in an amount of from about 0.05 to about 1 wt. percent of the reaction product mixture.

19. The method of claim 18 wherein the metal alkoxide and/or metal carbonate catalyst is present in an amount of from about 0.25 to about 0.75 wt. percent of the reaction product mixture.

20. The method of claim 19 wherein the metal alkoxide and/or metal carbonate catalyst is present in an amount of from about 0.40 to about 0.60 wt. percent.

21. The method of claim 14 wherein the organic catalyst is present in an amount of from about 0.05 to about 1.00 wt. percent of the reaction product mixture.

22. The method of claim 21 wherein the organic catalyst is present in an amount of from about 0.25 to about 0.75 wt. percent of the reaction product mixture.

23. The method of claim 22 wherein the organic catalyst is present in an amount of from about 0.40 to about 0.60 wt. percent of the reaction product mixture.

24. The method of claim 1 wherein the non-polar solvent is one or more solvents selected from the group consisting of benzene, toluene, xylenes, aromatic mixed solvents, pentanes, hexanes, heptanes, octanes, nonanes, decanes and petroleum distillate fractions.

25. The method of claim 24 wherein the aromatic mixed solvents are selected from the group consisting of aromatic 100, aromatic 150, aromatic 150ND, alkyl naphthalenes, cumene, alkyl benzenes.

26. The method of claim 24 wherein the petroleum distillate fractions are selected from the group consisting of petroleum ether, ligroin, napthas, gasoline fractions and kerosene and mixtures thereof.

27. The method of claim 24 wherein the nonpolar solvent is present in an amount of from about 95 to about 5 wt. percent of the reaction product mixture.

28. The method of claim 1 wherein the extraction temperature is at least about 50° C.

29. The method of claim 1 wherein the extraction temperature is at least about 60° C.

30. The method of claim 1 wherein the extraction temperature is at least about 70° C.

31. The method of claim 1 wherein the salt of the aqueous salt solution is at least one monovalent or divalent salt of mineral acids.

32. The method of claim 31 wherein the aqueous salt solution is present in an amount of from about 90 to about 0.1 wt. percent of the reaction product mixture.

33. The method of claim 1 wherein the pH is adjusted to less than about 5.

34. The method of claim 1 wherein the pH is adjusted to less than about 4.

35. The method of claim 1 wherein the pH of the reaction product mixture is adjusted to below 7 with at least one acid.

36. The method of claim 1 wherein the acid used to adjust the pH is at least one acid selected from the group consisting of hydrochloric acid, sulfuric acid, nitric acid, phosphoric acid.

37. The method of claim 36 wherein the acid is present in an amount sufficient to lower the pH to less than 7.

38. The method of claim 1 further comprising repeating one or more of the method steps of (a)-(f) at least one time.

39. The method of claim 38 further comprising adding a metal silicate absorbent to the separated organic phase.

40. The method of claim 39 wherein the metal silicate absorbent is of the general formula $xMO:ySiO_2:zH_2O$ wherein M is any metal of Group IA, IIA or IIIA of The Periodic Table, x and y are in a molar ratio of from about 1:1.5 to about 1:3.6 and z is equal to x.

41. The method of claim 40 wherein in the formula of the metal silicate absorbent, x is 1, y is 2.6 and z is 1.

42. The method of claim 40 wherein the metal in the metal silicate absorbent is magnesium, Ca, Ba, Na, Al.

43. The method of claim 41 wherein the metal in the metal silicate absorbent is magnesium, Ca, Ba, Na, Al.

44. The method of claim 39 further comprising vacuum stripping residual water from the reaction mixture wherein the vacuum stripping is conducted at from about 50 to about 110° C. and at less than about 100 mm Hg until the organic phase is dry.

45. The method of claim 44 further comprising adding from about 0.25 to about 2.5 wt. percent of a filter aid.

46. The method of claim 45 wherein the filter aid is selected from the group consisting of Celite® 545 (95% $SiO_2$) diatomoaceous earth, diatomite, kieselguhr and soda ashflux calcined.

47. The method of claim 46 wherein the dried organic phase and filter aid is filtered to obtain a hydroxyalkyl amide composition.

48. The method of claim 1 wherein the hydroxyalkyl amide composition contains any monofunctional or difunctional hydroxyalkyl amide.

49. The method of claim 48 wherein the hydroxyalkyl amide composition contains from about 10 to about 99 wt. percent of monofunctional or difunctional hydroxyalkyl amide.

50. The method of claim 48 wherein the hydroxyalkyl amide composition contains from about 40 to about 90 wt. percent of monofunctional or difunctional hydroxyalkyl amide.

51. The method of claim 48 wherein the hydroxyalkyl amide composition contains from about 70 to about 80 wt. percent of monofunctional or difunctional hydroxyalkyl amide.

52. The method of claim 1 wherein the hydroxyalkyl amide has a level of residual alkanolamine that is not greater than about 0.5 wt. percent.

53. The method of claim 1 wherein the hydroxyalkyl amide has a level of residual alkanolamine that is not greater than about 0.2 wt. percent.

54. The method of claim 1 wherein the hydroxyalkyl amide has a level of residual alkanolamine that is not greater than about 0.1 wt. percent.

55. The method of claim 1 wherein the hydroxyalkyl amide composition that has a level of residual catalyst that is reduced by about at least 50 percent.

56. The method of claim 1 wherein the hydroxyalkyl amide composition that has a level of residual catalyst that is reduced by about at least 75 wt. percent.

57. The method of claim 1 wherein the hydroxyalkyl amide composition that has a level of residual catalyst that is reduced by about at least 99 wt. percent.

58. The method of claim 1 wherein steps (a)-(f) are conducted over a period of from about 30 minutes to about 24 hours.

59. The method of claim 1 wherein steps (a)-(f) are conducted over a period of from about 4 to about 8 hours.

60. A method for the purification of the reaction product mixture of at least one alkanolamine and at least one ester and/or fatty natural material, wherein the parent alkanol of the ester contains from 1 to about 10 carbon atoms, optionally, in the presence of catalyst, and reaction product mixture containing a significant amount of residual alkanolamine and/or residual catalyst, which comprises providing said reaction product mixture, and either simultaneously or sequentially, in any particular order:
(a) adding at least one non-polar solvent to said reaction product mixture;
(b) heating said reaction product mixture to a desired extraction temperature;
(c) providing aqueous salt solution to said reaction product mixture;
(d) adjusting the pH of the reaction product mixture to below 7.0;
(e) allowing separation of the reaction product mixture into an organic phase and an aqueous phase after completion of steps (a)-(d); and
(f) removing the aqueous phase to produce a hydroxyalkyl amide composition with a reduced level of residual alkanolamine and/or residual catalyst.

61. The method of claim 60 wherein the ester is a fatty acid methyl ester or mixture of fatty acid methyl esters.

62. The method of claim 60 wherein the parent acid of the ester is a fatty acid derived from canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixtures thereof.

63. The method of claim 60 wherein the fatty natural material si selected from the group consisting of canola oil, castor oil, cocoa butter, coconut oil, cotton seed oil, olive oil, palm kernel oil, palm kernel (olein), palm kernel (stearine), peanut oil, rapeseed oil, safflower oil, soybean oil, sunflower oil, tall oil, corn oil, butter, lard, tallow, yellow grease, blubber, herring, menhaden, sardine oil, babasso oil and mixture thereof.

64. The method of claim 60 wherein the parent acid of the ester is selected from the group consisting of butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, steric, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15, 19-docosapentaenoic, docosahexaenoic, lignoceric, tetracosenoic and mixtures thereof.

65. The method of claim 60 wherein the parent alkanol of the ester is methanol.

66. The method of claim 60 wherein the non-polar solvent is selected from the group consisting of benzene, toluene, zylenes, aromatic mixed solvents, pentanes, hexanes, heptanes, octanes, nonanes, decanes and petroleum distillate fractions.

67. The method of claim 60 further comprising repeating one or more of the method steps of (a)-(f) at least one time.

68. The method of claim 60 further comprising vacuum stripping residual water from the reaction mixture.

69. The method of claim 60 wherein the vacuum stripping is conducted at from about 50 to about 110° C. and at less than about 100 mm Hg until the organic phase is dry.

70. The method of claim 60 wherein the alkanolamine is of the general formula RNHR' wherein R and R' is hydroxylalkyl of from 2 to about 10 carbon atoms.

* * * * *

UNITED STATES PATENT AND TRADEMARK OFFICE
CERTIFICATE OF CORRECTION

PATENT NO. : 7,312,346 B2 Page 1 of 1
APPLICATION NO. : 10/712830
DATED : December 25, 2007
INVENTOR(S) : Lambert et al.

It is certified that error appears in the above-identified patent and that said Letters Patent is hereby corrected as shown below:

Column 3, lines 22-23, "with ester are the same" should read --with the ester are the same--.

Column 3, line 26, "can be fatty acid amide" should read --can be a fatty acid amide--.

Column 13, line 21, Claim 40, "1:1.5" should read --1.5:1--.

Signed and Sealed this

Tenth Day of June, 2008

JON W. DUDAS
*Director of the United States Patent and Trademark Office*